(12) United States Patent
Varjonen et al.

(10) Patent No.: US 7,588,369 B2
(45) Date of Patent: Sep. 15, 2009

(54) IDENTIFICATION OF DETECTOR UNITS IN X-RAY IMAGING

(75) Inventors: Vesa Varjonen, Hyvinkää (FI); Jouni Onnela, Helsinki (FI)

(73) Assignee: PaloDEx Group Oy (FI)

( * ) Notice: Subject to any disclaimer, the term of this patent is extended or adjusted under 35 U.S.C. 154(b) by 669 days.

(21) Appl. No.: 10/561,564

(22) PCT Filed: Jun. 16, 2003

(86) PCT No.: PCT/FI03/00484

§ 371 (c)(1),
(2), (4) Date: Apr. 24, 2006

(87) PCT Pub. No.: WO2004/112446

PCT Pub. Date: Dec. 23, 2004

(65) Prior Publication Data

US 2006/0285637 A1    Dec. 21, 2006

(51) Int. Cl.
*A61B 6/14* (2006.01)
(52) U.S. Cl. ........................................ 378/191; 378/116
(58) Field of Classification Search ............. 378/38–39, 378/114–117, 98.5, 168, 191, 102
See application file for complete search history.

(56) References Cited

U.S. PATENT DOCUMENTS 6,295,337 B1 *  9/2001  Thevenin et al. ............. 378/117
6,402,743 B1    6/2002  Orszulak et al.
2004/0064027 A1 *  4/2004  Zimmermann et al. ...... 600/407

FOREIGN PATENT DOCUMENTS

WO    WO-0241783      5/2002
WO    WO-02/065935    8/2002

OTHER PUBLICATIONS

International Preliminary Report dated Sep. 26, 2005.
Database WPI, Week 200336, Derwent Publication JP 2002 191586, Canon KK, Jul. 9, 2002, Abstract.
Patent Abstracts of Japan, vol. 2002, No. 11, Nov. 6, 2002, JP 2002 191586, Canon, Inc., Abstract.

* cited by examiner

*Primary Examiner*—Hoon Song
(74) *Attorney, Agent, or Firm*—Andrus, Sceales, Starke & Sawall, LLP

(57) ABSTRACT

The invention concerns a device for identification of a detector unit in an X-ray imaging apparatus. For this purpose there is a detector unit (1a or 1b or 1c . . . ), selected from a group (10) of different detector array units (1a, 1b, 1c . . . ), and a transmitter-receiver (8) at side(s) of a space (V) for said object or a rack for storing those detector units belonging to said group. Recognition means (11) or a sensor units capable of detecting presence and absence of the detector units is also provided, as well as a communication line (2) for providing identification data concerning the presence (P2) or absence of a single detector unit in a predetermined volume or place.

9 Claims, 5 Drawing Sheets

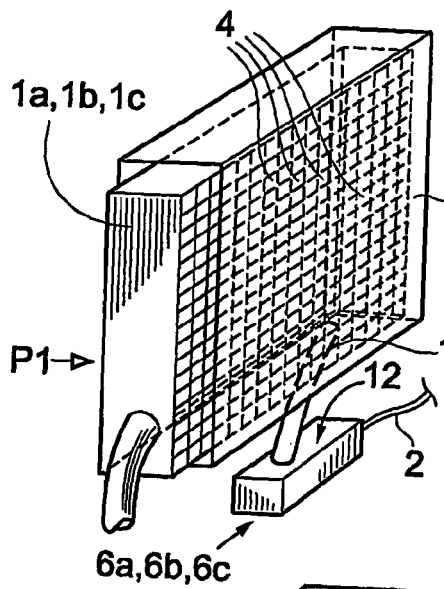
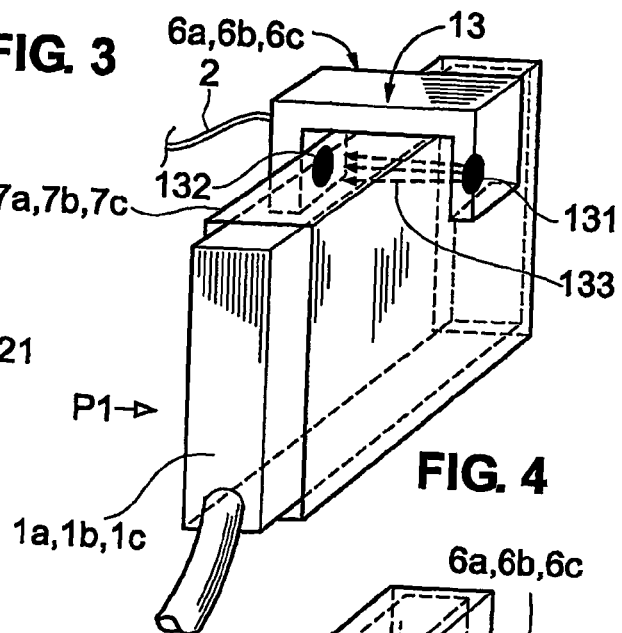
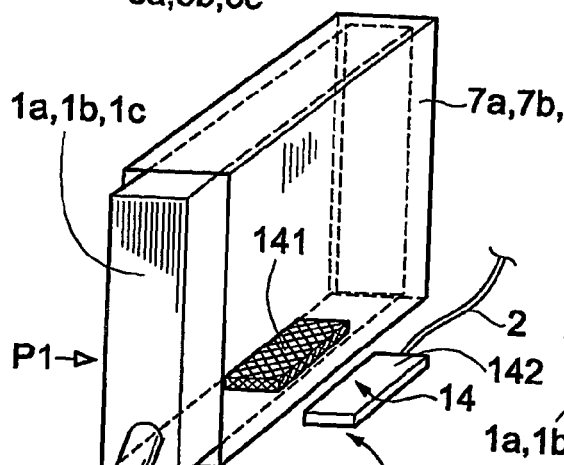
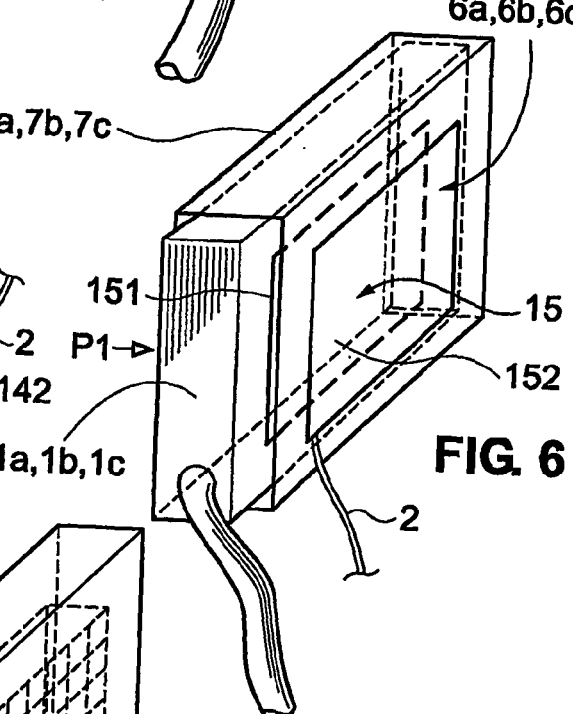
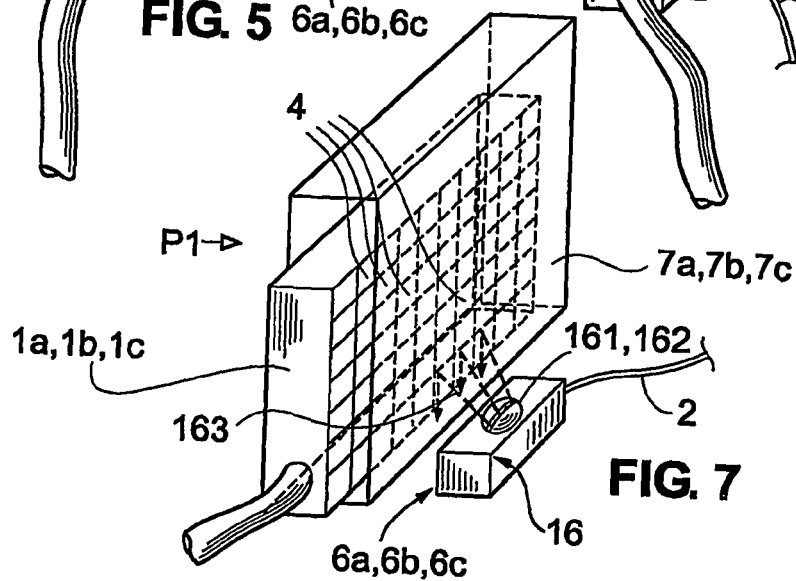

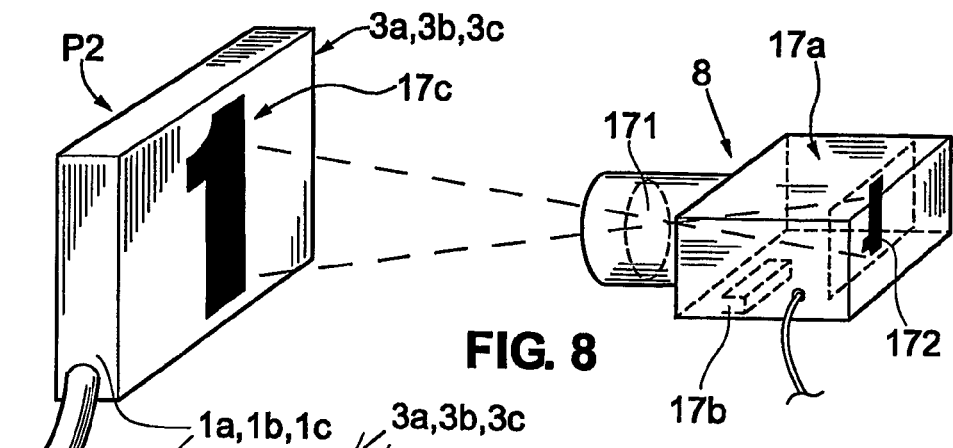
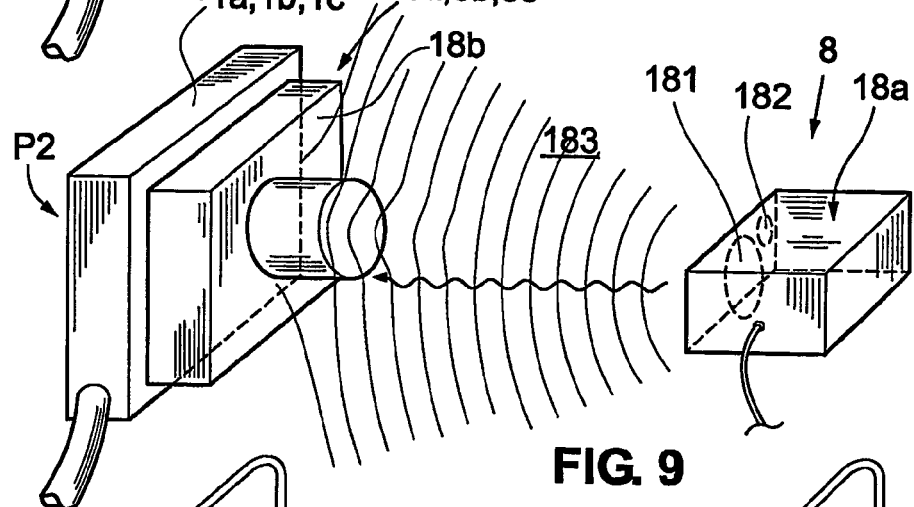
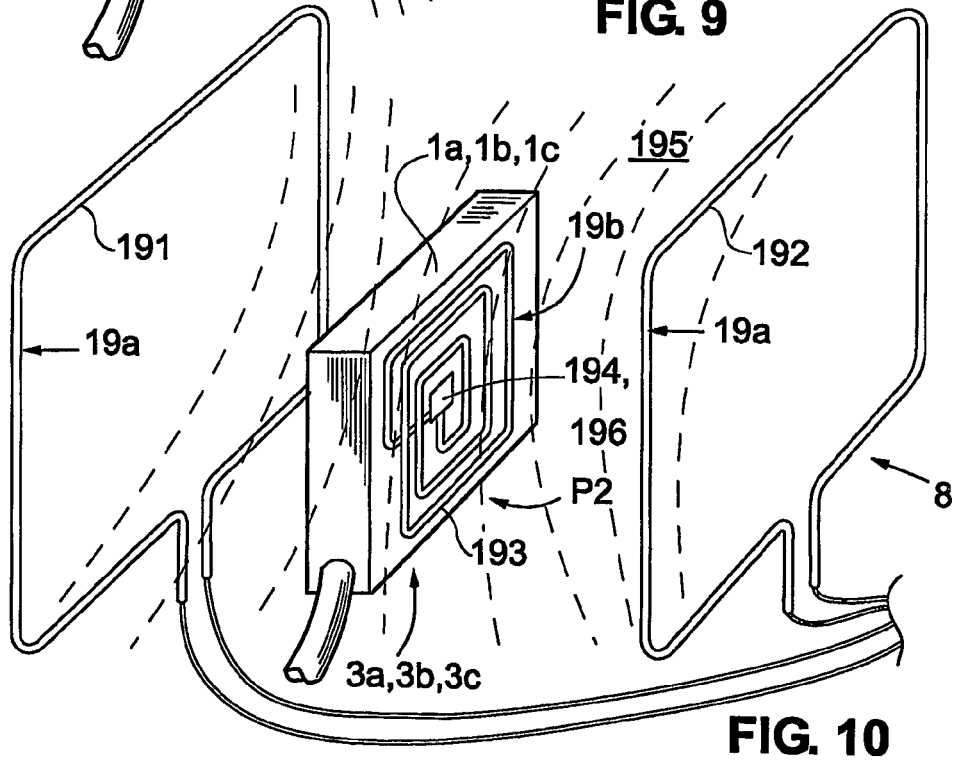

IDENTIFICATION OF DETECTOR UNITS IN X-RAY IMAGING

CROSS REFERENCE TO RELATED APPLICATION

The present application is the U.S. national stage application of International Application PCT/FI2003/000484, filed Jun. 16, 2003, which international application was published on Dec. 23, 2004 as International Publication WO 2004/112446.

FIELD OF THE INVENTION

The invention relates to a device for identification of a detector unit in an X-ray imaging apparatus provided with: a detector unit, selected from a group of different detector units, and adapted for positioning to receive an image-forming X-ray radiation after passing a human or animalian object, said detector unit being a detector array with a plurality of detector pixels; a reading unit connected to the detector unit and provided with means for processing the signals from said pixels of the detector unit and means for determining the position data of the pixels in said array while reading said signals. The invention also relates to a method for identification of a detector unit in an X-ray imaging apparatus adapted to utilize one detector unit of several detector units selectively for providing image data from an object through X-ray radiation.

BACKGROUND OF THE INVENTION

In X-ray imaging, when electrical detector units, i.e. detector arrays having a plurality of image forming pixels, like CCD-cells or CMOS-cells are used for transforming the X-ray radiation passed through the object to electrical signal, it is ordinary praxis that at least two, and several if necessary, different detector units are used. The different detector units are typically of different size having a greater or a smaller number of pixels, i.e. various number of X-ray radiation sensitive elements, whereupon the data flow for defining the position of each individual pixel in the detector unit and the actual signal that depends on the received radiation intensity from each individual pixel shall be coupled, which is performed by utilizing a clock frequency, i.e. the data is read from the detector arrays using a multiplexing. The different detector units can also have different other properties requiring e.g. greater or smaller gain or amplification of the output signals, or other deviating electrical settings. When the operating person selects a detector unit for a specific imaging task, it shall be also taken care that the correct clock frequency and the correct gain is selected or activated in the electronic device, typically a computer, to which the detector unit is connected. The operator can of course, do this selection/activation manually, but there is an evident risk that the operator forgets to do this or makes an error by feeding wrong setting.

It is the main object of the invention is to attain a device and/or a method, by which the human errors mentioned above, can be avoided. Accordingly, the intention is to find means to ensure that the correct settings for the individual detector unit selected for use are always fed into the computer, or a respective electronic device, utilized for reading the detector unit. Further object of the invention to attain a device and/or a method, which is as uncomplicated as possible, and could be added in the existing X-ray apparatuses without problems.

SUMMARY OF THE INVENTION

The problems described above can be overcome and the objects defined above can be reached by the device according to the invention, and by the method according to the invention.

According to the first aspect of the invention the device comprises: a rack for storing those detector units belonging to said group; a predetermined slot in the rack for each individual detector unit; a sensor unit in each of said slots capable of detecting presence and absence of the detector units in their predetermined slots; and a communication line between said sensor unit and said reading unit providing identification data concerning at least the absence of a single detector unit from its slot in the rack into said reading unit.

According to the second aspect of the invention the device comprises: a transmitter-receiver unit in an X-ray head, or at side(s) of a space for said object; recognition means in said transmitter-receiver unit capable of detecting presence and absence of the detector units in said space; a response unit with identity carrying means in each of said detector units; and a communication line between said transmitter-receiver unit and said reading unit providing identification data concerning the presence of a single detector unit in said space into said reading unit.

According to the third aspect of the invention the method comprises the steps of: providing at least two detector units available in a rack; selecting one of said at least two detector units and inserting it into an imaging X-ray radiation receiving position; reading an identification data from said rack respective to an absence of said one detector unit from said rack; and feeding data files corresponding said absent detector unit and forwarded on the basis of said identification data to a reading unit, which operates at least for reading image data from the detector unit.

According to the fourth aspect of the invention the method comprises the steps of: providing at least two detector units available; selecting one of said at least two detector units and moving it into an imaging X-ray radiation receiving position within a space for said object; reading remotely an identification data from said one detector unit present in said space; and feeding data files corresponding said present detector unit and forwarded on the basis of said identification data to a computer unit, which operates at least for reading image data from the detector unit.

BRIEF DESCRIPTION OF THE DRAWINGS

The foregoing summary, and the following detailed description of the preferred embodiments of the present invention, will be better understood when read in conjunction with the accompanying drawings, in which:

FIG. 3 to 7 represents schematically various sensor units, which can be used in the first embodiment of the device according to the invention to detect which one of the detector units is taken away from the storage rack into use. FIG. 3 also represent a detector unit that have a larger sensitive area and smaller pixel size, and FIG. 7 represent a detector unit that have a smaller sensitive area and larger pixel size.

FIG. 8 to 10 represents schematically various transmitter-receiver units, which can be used in the second embodiment of the device according to the invention to detect, which one of the detector units is within the space specified for use.

DETAILED DESCRIPTION OF THE PREFERRED EMBODIMENTS

Figure 1:
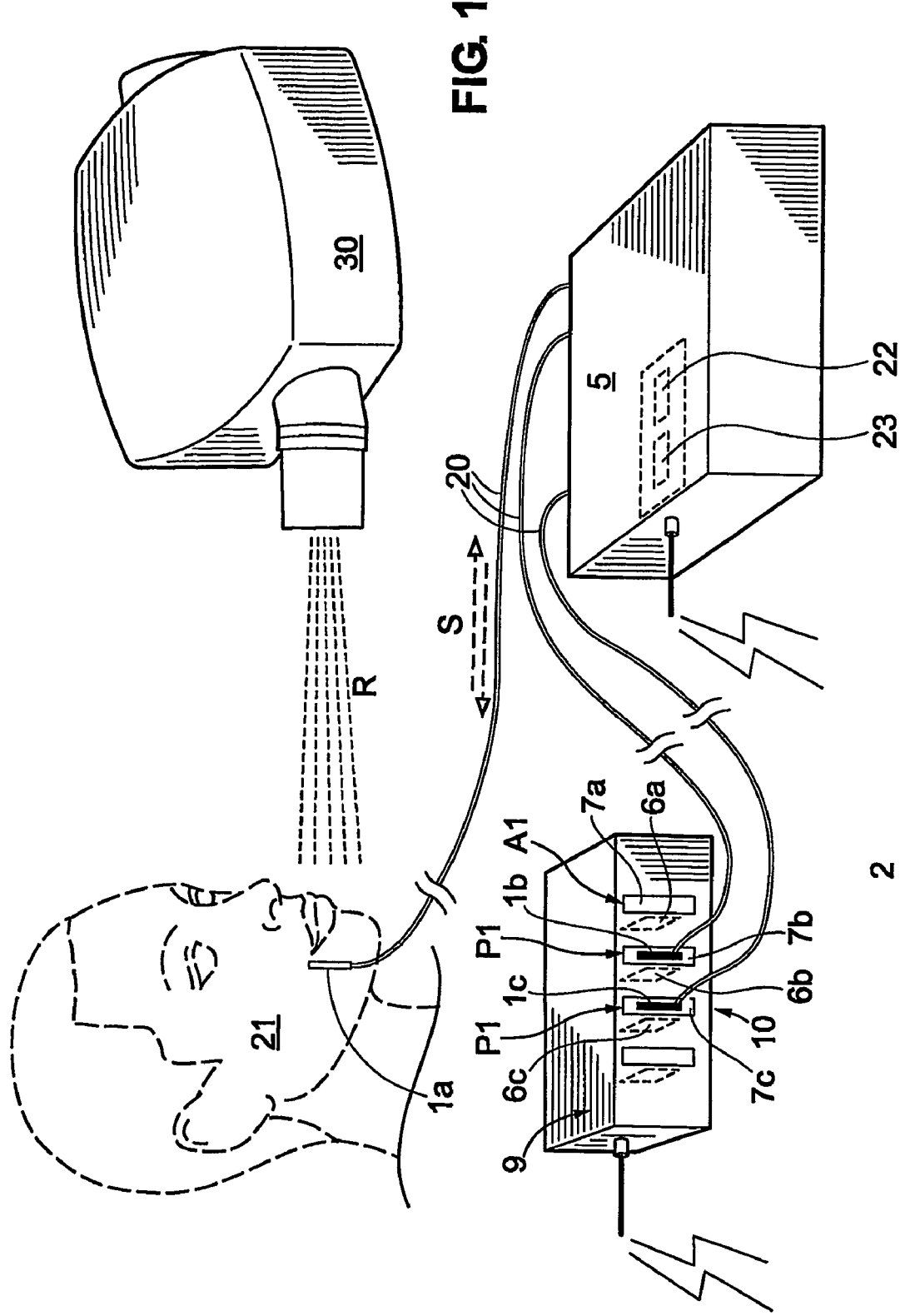
FIG. 1 represents schematically an X-ray imaging apparatus and a group of detector units as well as an electronic device for reading and processing the data from the detector unit positioned to receive radiation coming through an object, which X-ray apparatus is provided with the first embodiment of the device according to the invention for identification of a detector unit under use.
Figure 2:
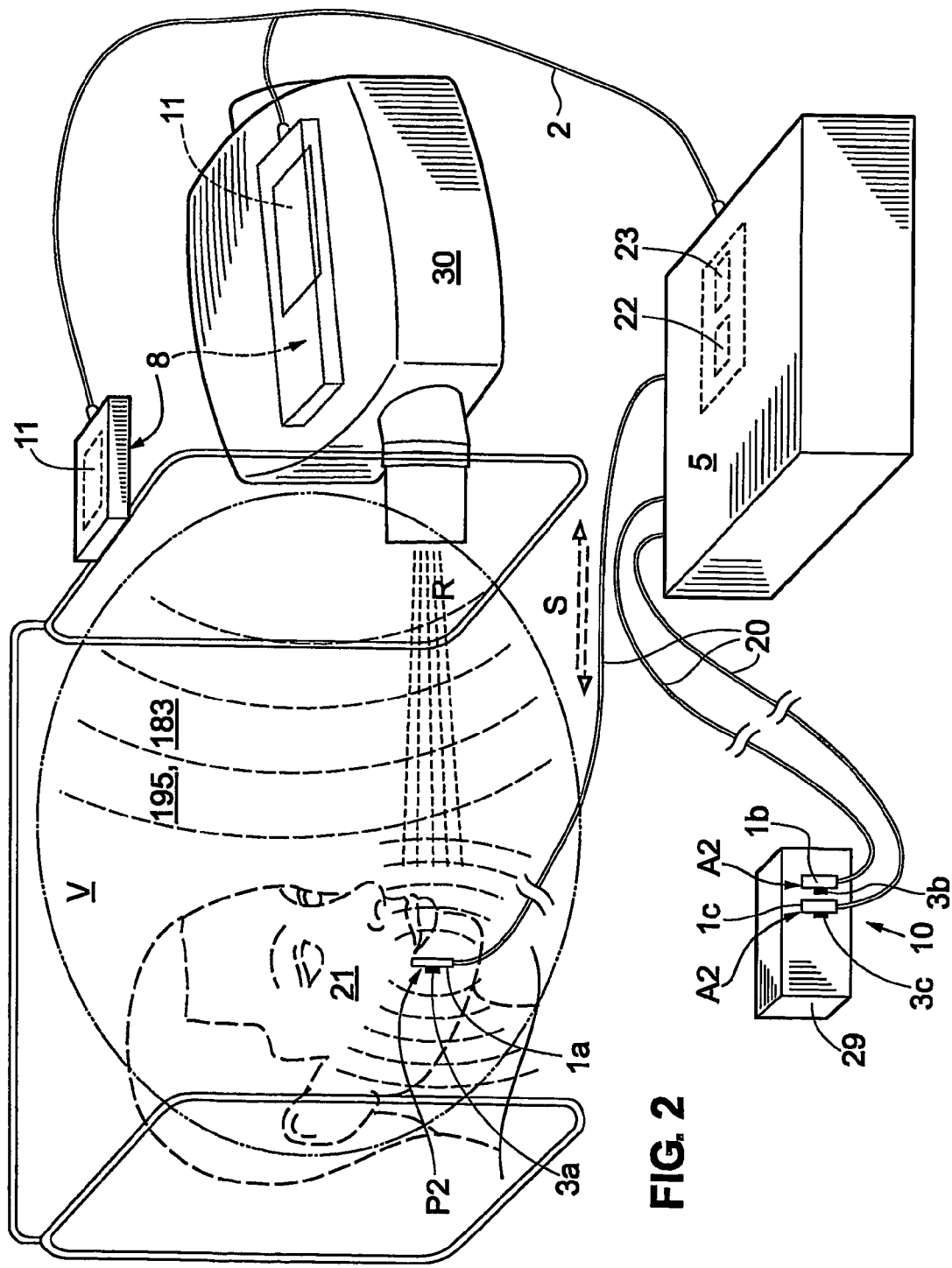
FIG. 2 represents schematically an X-ray imaging apparatus and a group of detector units as well as an electronic device for reading and processing the data from the detector unit positioned to receive radiation coming through an object, which X-ray apparatus is provided with the second embodiment of the device according to the invention for identification of a detector unit under use.

FIGS. 1 and 2 show X-ray imaging apparatuses generally. An X-ray apparatus is provided with an X-ray head 30 with an X-ray source, and arranged to radiate an image forming X-ray radiation R beam through a human or animalian object 21. The imaging target, not shown in the figures, is inside the object 21, and can be e.g. the teeth or jaw or any bone of the patient, or a lesion or lesions, like suspected tumor or cancer, in a soft tissue of the patient, as can be readily understood. The apparatus is further provided with a detector unit 1a or 1b or 1c..., selected from a group 10 of different detector units 1a, 1b, 1c. The individual detector unit selected is then positioned in a place, where it receives said image-forming X-ray radiation after passing said human or animalian object, or a part thereof. In the embodiments of FIGS. 1 and 2 the detector unit is to be positioned in the mouth of the patient in order the attain an image about the teeth and/or jaw of the patient, but for attaining images from other kind of targets the detector unit can be positioned behind that body portion of the patient, which contain the target in question.

The detector units 1a, 1b, 1c etc. are detector arrays, e.g. commercially available or specifically designed and manufactured CCD-cells or CMOS-cells or any new type of cell, with a plurality of detector pixels 4 arranged side by side to form an radiation sensitive area for image forming. In this case the cells can be based on amorphous silicon, selenium, CdTe, or CdZnTe, but the mentioned materials shall not be considered limiting the scope of the invention. Each pixel 4 in the array transforms the radiation falling on it into an electrical signal, which is typically proportional to the radiation intensity at that point. FIGS. 3 and 7 show simplified pixel configurations of the detector units, whereupon it shall be understood that the actual detector units include thousands of pixels. For different purposes there shall be available detector units having different widths and/or different heights for the radiation sensitive area, which means either different number of pixels and/or different sizes of pixels. The internal structure and materials of the individual pixel elements can be different, too, depending on the manufacturer, on the designed purpose etc. leading to different radiation detection and pixel reading properties. Accordingly, there are several different types of detector units, which can be selected for use, and typically at least two different detector units in the group 10 of detector units to be selected by the operating personnel for each individual imaging task. As can be understood, each different detector unit requires different settings when the signals created by the radiation in the pixels is to be read, so as to attain a correct interrelationship between each pixel position in the radiation sensitive area and the signal from each pixel, and to attain a correct signal level for further processing. Data concerning the pixel positions together with data concerning the signal from radiation intensity can be called image data, as an overall or common definition. The settings for reading the image data shall be matched with properties of that individual detector unit, which is selected by the operating personnel from the group 10. The present invention is directed just to ensuring that the correct settings are every time selected, too, when any of those detector units available and belonging to the detector unit group 10 are selected. It shall be noted that the detector units 1a, 1b, 1c etc. for detector unit group 10 are selected prior to introduction of the X-ray apparatus. This preselection of the detector units for the detector unit group can be done by the manufacturer of the X-ray apparatus, though the detector units belonging to the group can be changed later, but in both cases the settings requires their installation in the reading unit 5 prior to actual use. The invention does neither concern this preselection nor this installation, but the selection of the detector units from the group 10 having at least two preselected detector units and their respective settings installed so that the settings can be selected, too.

The X-ray apparatus is also provided with a reading unit 5 connected to the detector unit in use, according to the invention connected via signal cables 20, or some kind of wireless connection generally known, but not shown in the figures, to every detector unit 1a, 1b, 1c etc. that is arranged to be available, i.e. belong to the group 10 of detector units, for selecting by the operating personnel, as explained above. The reading unit 5 comprises means for processing the image data signals S from said pixels of the detector unit, and means for determining the position of the pixels in said array while reading said signals. The reading unit 5 also comprises memory means 22 for storing the settings necessitated for reading the image data from any of those detector units 1a, 1b, 1c . . . belonging to the group 10 of detector units. Accordingly, there is a specific data file DF1, DF2, DF3 etc. with the respective settings for each detector unit, which can be selected by the operating personnel for taking images from the object. The data file or a combination of data files typically incorporates at least individual clock-gain data files, each of which being specific to a detector unit in said group.

According to the invention the device for identification of a detector unit selected from the group 10 comprises identification data for each individual detector unit 1a, 1b, 1c etc. of the detector unit group 10, and means for giving a response or a information into the reading unit 5 concerning, which one of the identified detector units is taken into use by the operating personnel. The response or information is given either about the presence P2 of the detector unit 1a or 1b or 1c etc. inside the predetermined space V for the object 21, or about the absence A1 of the detector unit 1a or 1b or 1c etc. from the predetermined slot 7a, 7b, 7c etc. in a rack 9 for standby storage of the detector units. The response or information also comprises the identification data concerning that individual detector unit, which gives the response or information, or about which the response or information is given. The transferred identification data tells the reading unit, which one of the installed settings shall be used for reading the image data and for further processing thereof. For this purpose the reading unit 5 further comprises calculation means 23, which employs that one of the specific data files DF1, DF2, DF3 . . . , which includes the settings, corresponding to the detector unit, from which the identification data in the absence A1 of the single detector unit from the slot is received, or from which the identification data in the presence P2 of the single detector unit in the space V is received, for said pixel signal processing and said pixel position data determining. The means how the identification data about the absence A1 from the slot and how the identification data about the presence P2 in the space is transmitted into the reading unit 5 is described in detail later in this text.

The identification data concerning each detector unit can be as simple as a 1-bit data, i.e. can have only two values ON and OFF, which is the same for all detector units in the group 10. This alternative can be used in cases, where each sensor unit 6a, 6b, 6c etc. for the detector units is directly and nondetachably coupled with the respective data file of each detector unit in the memory means 22. This can be exemplified by a hardware circuit, in which the data files for each detector unit are stored e.g. in a separate EPROM memory, whereupon one of the 1-bit data having a value ON—meaning for instance that a detector unit is taken away from its slot in the rack—actually is a switching on of one of the switches 12-16. Here the switch connects through electrical wiring the EPROM storing the data file of the detector unit taken away into the calculation means 23. This first alternative is applicable and preferred for the embodiments of FIGS. 1 and 3 to 7. The identification data concerning each detector unit can typically be a numerical or a alphabetical data, too, like numbers 1, 2, 9745, or letters A, B, BZC, or a combination of these, resemble so called serial numbers, or any surface structure or configuration without a name like ornament, or any chain of bits, like 0110010, individual for each single detector unit in the group 10. This second alternative is applicable and preferred for the embodiments of FIGS. 2 and 8 to 10. The identification data concerning each detector unit can also be the settings, i.e. the specific data file for reading and/or further processing of the image data from the respective detector unit, partly or wholly. This third alternative requires more data transfer, and is possibly not so effective.

The first embodiment of the device for identification of the detector unit, which is in use during a specific instance, comprises a rack 9 for storing those detector units belonging to the group 10, and a predetermined slot 7a, 7b, 7c . . . in the rack for each individual detector unit 1a, 1b, 1c etc. The device further comprises a sensor unit 6a, 6b, 6c etc. in each of said slots capable of detecting presence P1 and absence A1 of the detector units in their predetermined slots, and a communication line 2 between all of the sensor units and the reading unit 5. The communication line 2 can be a wireless line, as shown in FIG. 1, like a radio wave or infrared or some other type of communication linkage operating over the space between the reading unit and the rack, being generally known. Sensor units 6a, 6b, 6c . . . provides identification data concerning at least the absence A1 of a single detector unit from its slot 7a or 7b or 7c . . . in the rack into said reading unit.

The sensor unit can be a mechanical contact switch 12, with ON-OFF characteristics, typically a monostable switch, having e.g. a spring loaded contact lever 121 moving by pressure of the detector unit. When a detector unit is taken away from its slot, meaning absence A1 of this detector unit, it no more presses the switch 12, which makes a contact in ON-state and provides on continuous electrical communication into the reading unit 5. This way the data file corresponding to that detector unit taken away is connected to use for the calculation means 23. When the other detector units are in their slots pressing constantly the respective mechanical switches, these switches 12 are in OFF-state, meaning presence P1 of these detector units.

The sensor unit can be an optical fork switch 13 with ON-OFF characteristics. This kind of switch typically comprises a light emitting diode 131 and a light sensitive diode 132 so positioned that the detector units can be pushed therebetween so as to interrupt the light beam 133, meaning presence P1, and taken away from between the diodes so as to retain the light beam, meaning absence A1.

The sensor unit can be a magnetic field switch 14 with ON-OFF characteristics, whereupon each detector unit is provided with e.g. a piece of magnetic material 141 and the slots are provided with magnetic field detectors 142, like Hall-elements. Stronger magnetic fields mean presence P1 of the detector units, and a weaker magnetic field means absence A1 of a detector unit.

The sensor unit can be a capacitive switch 15 with ON-OFF characteristics, whereupon the detector units are provided with first capacitor plates 151 and the slots are provided with second capacitor plates 152, there being a definite capacitance therebetween meaning presence P1, when the detector units are in their slots, and practically no capacitance meaning absence A1, when the detector unit is not in its slot. The different capacitances can be detected e.g. by a resonant oscillator circuit.

The sensor unit can also be an ultrasound switch 16 with ON-OFF characteristics, whereupon the switches are provided with sound sources 161 and sound receivers 162 directed independently to the interiors of each slot to be reflected from some of the outer surfaces of the detector units. When the detector units are in their slots sound signals 163 with shorter response time and high amplitude are received meaning presence P1, and when the detector unit is not its slots a sound signal 163 with longer response time and low amplitude is received meaning absence A1. A single frequency sound source is applicable here. In all other respect these latter sensor units 13 to 16 operates in the same way as the mechanical contact switch 12, as described above.

Not all of the above mentioned sensors have intrinsically ON-OFF states, but they are able to detect values proportional to another value. In spite of this, the sensor units can be designed to have the characteristics needed. In this embodiment every sensor unit in the slots 7a, 7b, 7c . . . of a rack 9 are similar or practically similar to each other, and the detector units 1a, 1b, 1c . . . are without any identification, but they are identified by their predetermined slots. The components for the sensors described above are commercially available, and any person skilled in the art is capable to design a respective sensor, and accordingly the construction and operation of these sensors are not described in detail.

The second embodiment of the device for identification of the detector unit, which is in use during a specific instance, comprises a transmitter-receiver 8 unit preferably in the X-ray head 30, i.e. somewhere at one side or two or several sides of the space V for the object 21, and recognition means 11 in said transmitter-receiver unit capable of detecting presence P2 and absence A2 of the detector units in a space V, in which the object 21 is to be placed, as well as a response unit 3a, 3b, 3c . . . with identity carrying means in each of said detector units 1a, 1b, 1c etc. The response units are, accordingly, part of the detector units. Here too, there is a communication line 2 between the transmitter-receiver unit and the reading unit 5 providing identification data concerning the presence P2 of a single detector unit in said space V into the reading unit 5. The communication line 2 can be a wired line, as shown in FIG. 2, like an electrical or optical or some other type of cable operating between the reading unit and the transmitter-receiver unit, being generally known.

The transmitter-receiver unit 8 and said response units 3a, 3b, 3c etc. form a combination concerning the method, by which they communicate with each other. The transmitter-receiver unit 8 can preferably be an electromagnetic field transmitter-receiver 19a, and a transponder 19b as said identity-carrying means, with ON-OFF characteristics. The most effective configuration of the electromagnetic field transmitter-receiver comprises two large-area antennas 191, 192 positioned at the sides of the space V as a gate, where the detector unit 1a, 1b, 1c is to be actually used. This way a strong enough electromagnetic field, i.e. radio wave field, with clear boundaries is attained using low-power radio transmitter. Anyway a so-called short-distance radio wave link is the system, which is used. The transponders 19b are generally RLC resonant circuits, each of which typically comprises a printed circuit coil 193 and resistor-capacitor-circuit or inductance-resistor-capacitor-circuit 194, whereupon for each separate transponder attached to different detector units have a different resonant frequency identifying the detector unit. The resonant frequency can be easily sensed by the recognition means 11, and when each of the frequencies is stored in the memory means 22 in connection with the data file DF1, DF2, DF3 . . . of the detector unit, in which the transponder in question is attached, the data file of that detector unit, whose responding frequency is sensed meaning presence P2 in the space, can be readily taken from the memory means for utilization by the calculation means. The responders 19b in those detector units, which are not in use and accordingly not within the space V, are outside the reach of the electromagnetic field 195, does not give a response that could be received by the transmitter-receiver unit 8, and accordingly are in absence A2. The presence P2 of a specific transponder and the respective detector unit is sensed through a power loss, like voltage or current drop, in the transmitter caused by the energy drawn by the resonant circuit of the transponder. This power loss can be found directly from the transmitter by a circuit, e.g. via a feed-back circuit, which acts as the receiver in this case, and the recognition means 11 senses the resonant frequency. If necessary the detector units not in use can be stored in a rack 29 built as a Faraday shield. In this alternative the transmitter-receiver unit 8 shall be a multi-frequency transmitter-receiver capable of handling frequencies over that range, within which the different resonant frequencies of the transponders exist. It is also possible to provide the transponder with a microchip 196 having an own radio wave receiver-transmitter and identification data carrying memory, together with printed circuit coil 193, which in this case acts as an antenna. In this alternative the two-antenna gate disclosed above may be replaced by a one-antenna system, and a single frequency transmitter-receiver can be used, because a substantially single frequency carries the identification data, depending on the type of modulation, of course.

The transmitter-receiver unit 8 can be an optical digital camera 17a having an objective 171 and a light sensitive imaging cell 172 known as such, which is provided with shape or color analyzing means 17b, and specific configuration or color 17c as said identity carrying means, with ON-OFF characteristics. The shape/configuration analyzing means are strongly developed lately, and any of these known or possible new programs applicable can be used. Color analysis is a much more simple task, and for the purpose there exists many alternatives that are useful. The shape, color and/or configuration forming the identification are positioned on the outer surface of the detector units 1a, 1b, 1c. The digital camera 17a, acting as the receiver, is preferably positioned on the X-ray head, and directed towards the space V. Available light, daylight and/or from room lighting is generally enough as a transmitter, no special illuminating means are normally necessitated. As can be understood, the presence P2 of a detector unit with a specific identification can be sensed by the camera and shape or color analyzing means 17b or a proper program, when it is in front of the camera. Other detector units not within the sight of the camera are of course in absence A2.

The transmitter-receiver unit 8 can also be an ultrasound sender-receiver 18a, e.g. some kind of loudspeaker 181 and a microphone 182 or a power loss sensing means, and specifically tuned resonators 18b as identity carrying means, with ON-OFF characteristics. Ultrasound with high enough frequency is practical, because the higher the frequency the more limited is the sound cone 183 from the sender forming effectively the space V, and because high frequencies well above 20 kHz allow tuned resonators having small size. Actually the sender shall be a multi-frequency sender, whereupon its sends frequencies over a range within which the resonant frequencies of the tuned resonators 18b are included. These resonators can be eg. Helmholz resonators, each having a specific resonant frequency and attached on the detector units. It can be understood that when one detector unit with a resonator 18b having a resonant frequency is in front of the ultrasound sender-receiver 18a, more specifically within the sound cone and so in presence P2, the resonator causes a drop of the sound intensity in that frequency, which drop can be received either by the microphone or through a power loss in the transmitter caused by the energy drawn by the resonant circuit of the transponder, analogous with the system described in the context of electromagnetic field transmitter-receive. Here too, the recognition means 11 senses the resonant frequency. Other detector units outside the sound cone are of course in absence A2.

Not all of the above mentioned sensors have intrinsically ON-OFF states, but they are able to detect values proportional to another value. In spite of this, the sensor units can be designed to have the characteristics needed. In this embodiment every response unit 3a, 3b, 3c etc. on the detector units 1a, 1b, 1c are different from each other. The components for the response units, i.e. for responders, transmitter-receiver 8 and recognition means 11 described above are commercially available, and any person skilled in the art is capable to design a respective sensor, and accordingly the construction and operation of these sensors are not described in detail.

Figure 11:
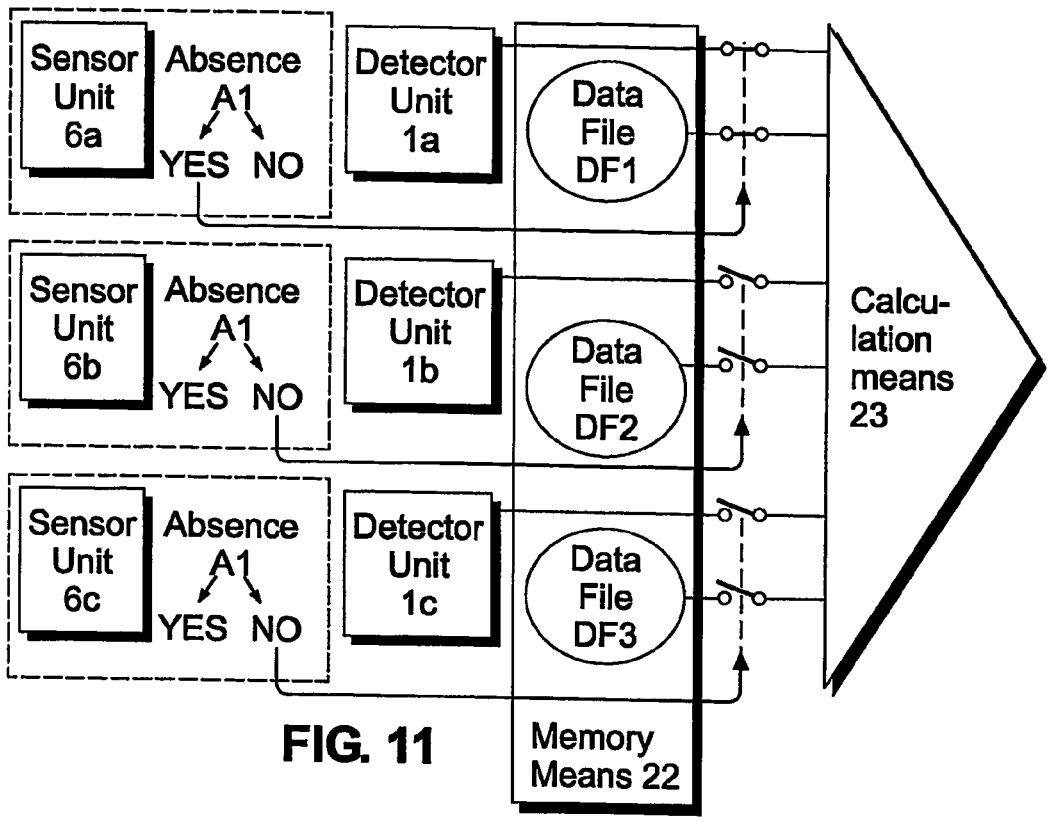
FIG. 11 represents schematically the connections and logics—using symbolic components—between the detector units, sensor units, memory means and the calculation means concerning the first embodiment of the device according to the invention.
Figure 12:
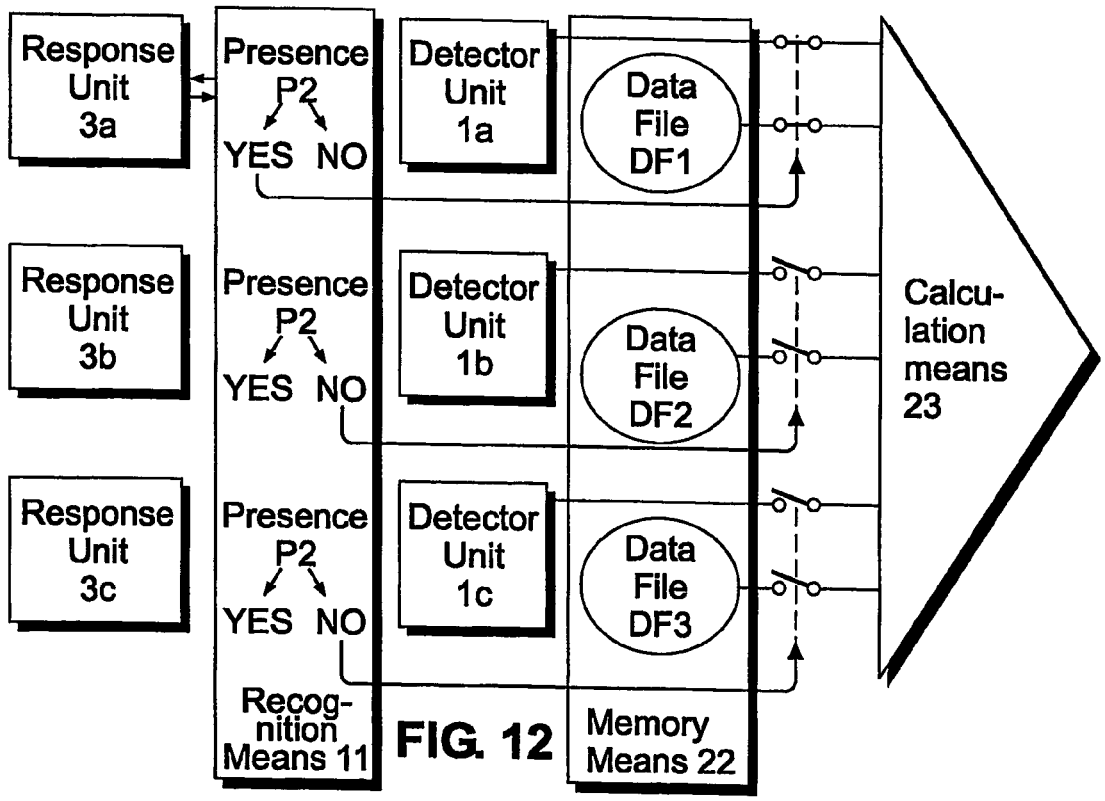
FIG. 12 represents schematically the connections and logics—using symbolic components—between the detector units, response units, recognition means, memory means and the calculation means concerning the second embodiment of the device according to the invention.

Accordingly, there are two alternatives for the method for identification of a detector unit in an X-ray imaging apparatus adapted to utilize one detector unit of several detector units selectively for providing image data from an object 21 through X-ray radiation R. At first it is providing at least two detector units 1a, 1b, 1c . . . available either in a rack 9 with the slots or from some other place, like the other rack 29. At second it is selected one 1a or 1b or 1c . . . of said at least two detector units, which belong to the group 10 of detector units, and inserted into an imaging X-ray radiation receiving position. According to the first alternative, the identification data is then read from said rack respective to an absence A of said one detector unit from said rack 9, more specifically from the predetermined slot, followed by feeding of the data files DF1, DF2, DF3 . . . corresponding to said absent A1 detector unit and forwarded on the basis of said identification data to a reading unit 5. According to the second alternative, an identification data from the selected detector unit within the space V for the object, and so present P2, is then read remotely, followed by feeding of the data files DF1, DF2, DF3 . . . corresponding to said absent A1 detector unit and forwarded on the basis of said identification data to a reading unit 5. The closed and open switches in FIGS. 11 and 12 describe, which of the individual data are fed and which not, only, and not the constructions of the device.

The invention claimed is:

1. A device for identification of a detector unit in an X-ray imaging apparatus provided with:
    a detector unit, selected from a group of different detector units, and adapted for positioning to receive an image-forming X-ray radiation after passing a human or animalian object, said detector unit being a detector array with a plurality of detector pixels;
    a reading unit connected to the detector unit and provided with means for processing the signals (S) from said pixels of the detector unit and means for determining the position data of the pixels in said array while reading said signals, characterized in that said device comprises:
    a rack for storing those detector units belonging to said group;
    a predetermined slot in the rack for each individual detector unit;
    a sensor unit in each of said slots capable of detecting presence (P1) and absence (A1) of the detector units in their predetermined slots; and
    a communication line between said sensor unit and said reading unit providing identification data concerning at least the absence (A1) of a single detector unit from its slot in the rack into said reading unit.

2. A device according to claim 1, characterized in that said sensor unit is:
    a mechanical contact switch with ON-OFF characteristics; or
    an optical fork switch with ON-OFF characteristics; or
    a magnetic field switch with ON-OFF characteristics; or
    a capacitive switch with ON-OFF characteristics; or
    an ultrasound switch with ON-OFF characteristics.

3. A device according to claim 1, characterized in that said reading unit comprises memory means for storing at least individual clock-gain data files (DF1, DF2, DF3 . . . ), each of which being specific to a detector unit in said group; and that said reading unit further comprises calculation means, which employs that one of the specific data files corresponding to the detector unit, from which said identification data in the absence (A1) thereof from the slot is received, for said pixel signal processing and said pixel position data determining.

4. A device for identification of a detector unit in an X-ray imaging apparatus provided with:
    a detector unit, selected from a group of different detector units, and adapted for positioning to receive an image-forming X-ray radiation after passing a human or animalian object, said detector unit being a detector array with a plurality of detector pixels;
    a reading unit connected to the detector unit and provided with means for processing the signals (S) from said pixels of the detector unit and means for determining the position data of the pixels in said array while reading said signals, characterized in that said device comprises:
    a transmitter-receiver at side(s) of a space (V) for said object;
    recognition means in said transmitter-receiver unit capable of detecting presence (P2) and absence (A2) of the detector units in said space (V);
    a response unit with identity carrying means at each of said detector units; and
    a communication line between said transmitter-receiver unit and said reading unit providing identification data concerning the presence (P2) of a single detector unit in said space (V) into said reading unit.

5. A device according to claim 4, characterized in that said transmitter-receiver unit and said response unit as a combination is:
    an optical digital camera with shape or color analyzing means, and specific configuration or color as said identity carrying means, with ON-OFF characteristics; or
    an ultrasound sender-receiver, and specifically tuned resonators as identity carrying means, with ON-OFF characteristics; or
    an electromagnetic field transmitter-receiver, and a transponder as said identity-carrying means, with ON-OFF characteristics.

6. A device according to claim 4, characterized in that said reading unit comprises memory means for storing at least individual clock-gain data files (DF1, DF2, DF3 . . . ), each of which being specific to a detector unit in said group; and that said reading unit further comprises calculation means, which employs that one of the specific data files corresponding to the detector unit, from which said identification data in the presence (P2) thereof within the space is received, for said pixel signal processing and said pixel position data determining.

7. A device according to claim 5, characterized in that electromagnetic field transmitter-receiver is a short distance radio wave link.

8. A method for identification of a detector unit in an X-ray imaging apparatus adapted to utilize one detector unit of several detector units selectively for providing image data from an object through X-ray radiation (R), characterized in that said method comprises the steps of:
    providing at least two detector units available in a rack;
    selecting one of said at least two detector units and inserting it into an imaging X-ray radiation receiving position;
    reading an identification data from said rack respective to an absence (A1) of said one detector unit from said rack; and
    feeding data files (DF1, DF2, DF3 . . . ) corresponding to said absent (A1) detector unit and forwarded on the basis of said identification data to a reading unit, which operates at least for reading image data from the detector unit.

9. A method for identification of a detector unit in an X-ray imaging apparatus adapted to utilize one detector unit of several detector units selectively for providing image data from an object through X-ray radiation (R), characterized in that said method comprises the steps of:
    providing at least two detector units available;
    selecting one of said at least two detector units and moving it into an imaging X-ray radiation receiving position within a space (V) for operation;
    reading remotely an identification data from said one detector unit present (P1) in said space (V) for operation; and
    feeding data files (DF1, DF2, DF3 . . . ) corresponding to said present (P2) detector unit and forwarded on the basis of said identification data to a reading unit, which operates at least for reading image data from the detector unit.

* * * * *

UNITED STATES PATENT AND TRADEMARK OFFICE
CERTIFICATE OF CORRECTION

PATENT NO. : 7,588,369 B2  Page 1 of 1
APPLICATION NO. : 10/561564
DATED : September 15, 2009
INVENTOR(S) : Varjonen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this

Fourteenth Day of December, 2010

David J. Kappos
*Director of the United States Patent and Trademark Office*